US00PP11914P2

(12) United States Plant Patent
Werner et al.

(10) Patent No.: US PP11,914 P2
(45) Date of Patent: Jun. 12, 2001

(54) PEACH TREE NAMED 'CHINA PEARL'

(76) Inventors: Dennis James Werner, 268 Kilgore Hall, Horticultural Science Department North Carolina State University; Steve Martin Worthington; Layne Karlton Snelling, both of 59 Kilgore Hall, Horticultural Science Department North Carolina State University, all of Raleigh, NC (US) 27695-7609

( * ) Notice: Subject to any disclaimer, the term of this patent is extended or adjusted under 35 U.S.C. 154(b) by 0 days.

(21) Appl. No.: 09/152,347

(22) Filed: Sep. 14, 1998

(51) Int. Cl.[7] ..... A01H 5/00
(52) U.S. Cl. ..... Plt./196
(58) Field of Search ..... Plt./195, 196

(56) References Cited

U.S. PATENT DOCUMENTS

P.P. 878 * 10/1949 Geheb ..... Plt./196
P.P. 8,195 * 4/1993 Zaiger et al. ..... Plt./196

* cited by examiner

*Primary Examiner*—Bruce R. Campell
*Assistant Examiner*—Wendy A. Baker

(57) ABSTRACT

A new and distinct variety of edible peach tree which has the following unique combination of desirable features that are outstanding in a new variety.

1. High flower bud chilling (cold) requirement resulting in later flowering relative to other commercial varieties of peach.
2. Flower buds which demonstrate a high level of resistance to cold temperature injury.
3. Firm, white flesh fruit with low levels of organic acids, resulting in fruit with a mild, sweet taste.
4. Heavy and regular bearing of large size fruit, up to 3½ inches in axial diameter.
5. Fruit with late maturity.

6 Drawing Sheets

SUMMARY OF THE INVENTION

The new and distinct variety of peach (*Prunus persica* (L.) Batsch) originated as a first generation descendant from a hand pollinated cross of 'Contender' peach (non-patented)×'Plant Introduction (PI) 134401' made in 1988 at the Sandhills Research Station at Jackson Springs, N.C. 'Contender' was released and named as a peach cultivar by the North Carolina Agricultural Research Service in 1987, and is available in commerce. The 'PI 134401' parent used in this hybridization was introduced into the United States from China in 1927, has not been named, and is unavailable in commerce.

Plants and fruit of this new variety differ phenotypically from its parents. The new variety produces large, white flesh fruit that are low in acid, differing from the yellow flesh, high acid fruit of 'Contender'. The round, smooth fruit have attractive red skin color, the foliage and fruit have moderate bacterial spot resistance, and the flowers and young fruit exhibit high resistance to freezing temperatures, distinguishing it from 'PI 134401'. Also, 'PI 134401' shows no red color on the fruit surface, the fruit is elongated and furrowed, and buds are sensitive to cold temperature.

The approximately 200 seeds resulting from this controlled hybridization were germinated in a greenhouse at North Carolina State University, Raleigh, N.C. in the Fall of 1988 and planted in the field in Spring of 1989. These trees, growing on their own roots, first produced fruit in 1991, and one seedling, designated NC-C5S-005, was selected for its large white flesh fruit, attractive red color, bacterial spot resistance, low acid fruit, and heavy fruit production. This original plant was growing on its own roots, and demonstrated characteristics identical to those subsequently expressed when propagated on 'Lovell' seedling rootstock.

During 1993 and 1994, the original plant selection was propagated asexually by grafting of vegetative buds onto the standard peach seedling rootstock, cultivar 'Lovell', at the Sandhills Research Station. Seven grafted trees of the variety were established in test plots at Sandhills Research Station in 1994, and sixty grafted trees of the variety were established at the same station in 1995.

The new variety has routinely been asexually multiplied by grafting, specifically 'T' budding. It readily forms a graft union with peach 'Lovell' rootstock and resumes normal growth. During all asexual propagation, the characteristics of the original plant have been maintained, grafted trees on 'Lovell' rootstock exhibit characteristics identical to those of the tree on its own roots, and no aberrant phenotypes have appeared.

Test planting and performance evaluation over seven years at the Sandhills Research Station demonstrate this variety to be consistent in its characteristics even under the different growing conditions associated with yearly climatic variation.

Plants of the new variety are very vigorous and grow rapidly after establishment of trees in the field. Young trees have averaged 2–3 feet of growth per year. Plants are semi-upright in growth habit, and possess willowy branches. Flowering sometimes occurs in the second year of growth, but more commonly trees begin flowering in the third year after establishment. Flowers are single, medium red-purple, showy, and very attractive. Flowering usually begins in mid to late March in Raleigh, N.C.; the chilling requirement is estimated to be 1100 hours below 4 C, based on comparison of flowering time to known varieties such as 'Contender' and 'Biscoe'. Flowering generally lasts for 7–10 days, depending on temperature at time of bloom.

Fertility of flowers is excellent, and fruit set is generally very high in most years. Flowers have shown excellent resistance to cold temperatures during winter dormancy and during flower development in the Spring. Trees produced 60% of a full fruit crop in 1996, a year in which all commercial varieties except 'Contender' failed to produce a fruit crop at the Sandhills Research Station because of low temperature injury. In that year, trees in flower were exposed to six consecutive nights of below freezing temperatures from March 9 through March 14, inclusive. Fruit are very large, often 7.6 to 8.9 cm in diameter, white fleshed, and low acid. Laboratory measurements of fruit at maturity show that acidity levels are about three-fold lower than that of 'Contender', the yellow flesh parent. Fruit ripen in late July to early August in Jackson Springs, N.C., averaging August 1 over 5 years of observation.

The new variety has been named the CHINA PEARL cultivar.

BRIEF DESCRIPTION OF THE PHOTOGRAPHS

Figure 1:
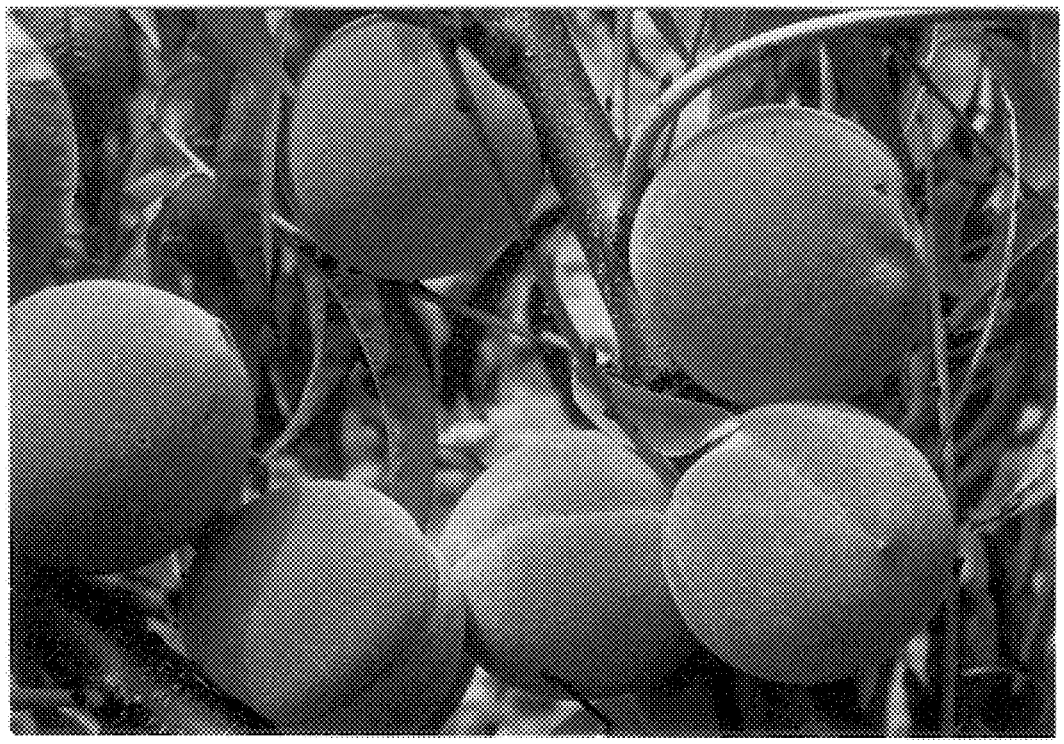
FIG. 1 shows typical specimens of the mature fruit of 'China Pearl' photographed on four-year-old trees on Aug. 11, 1998.
Figure 2:
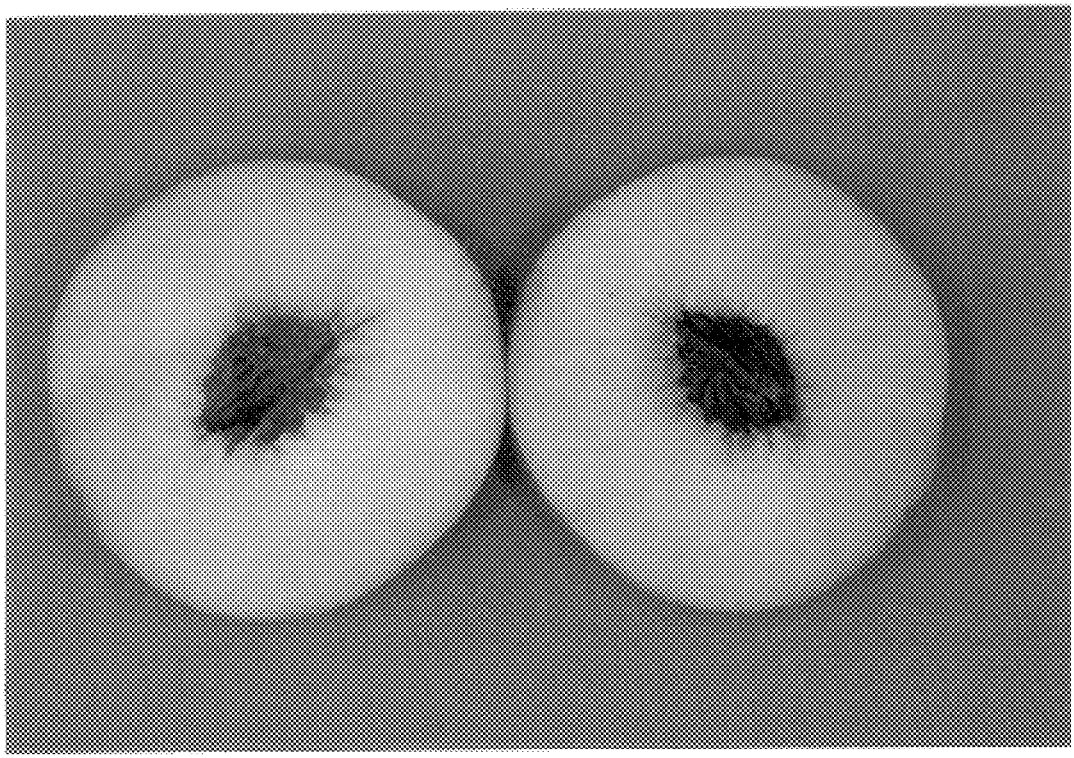
FIG. 2 shows a cross section of a typical fruit, showing the white flesh with minimal red pigmentation around the stone.
Figure 3:
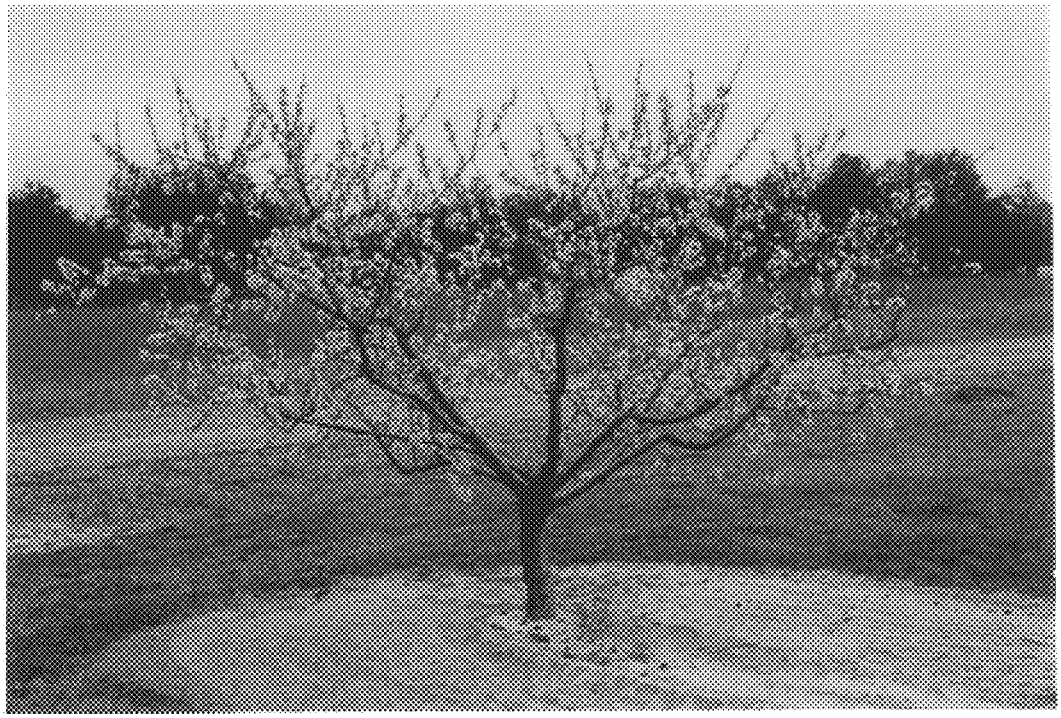
FIG. 3 shows the typical form and flower density of a seven-year-old tree of 'China Pearl' photographed on Mar. 17, 2000.
Figure 4:
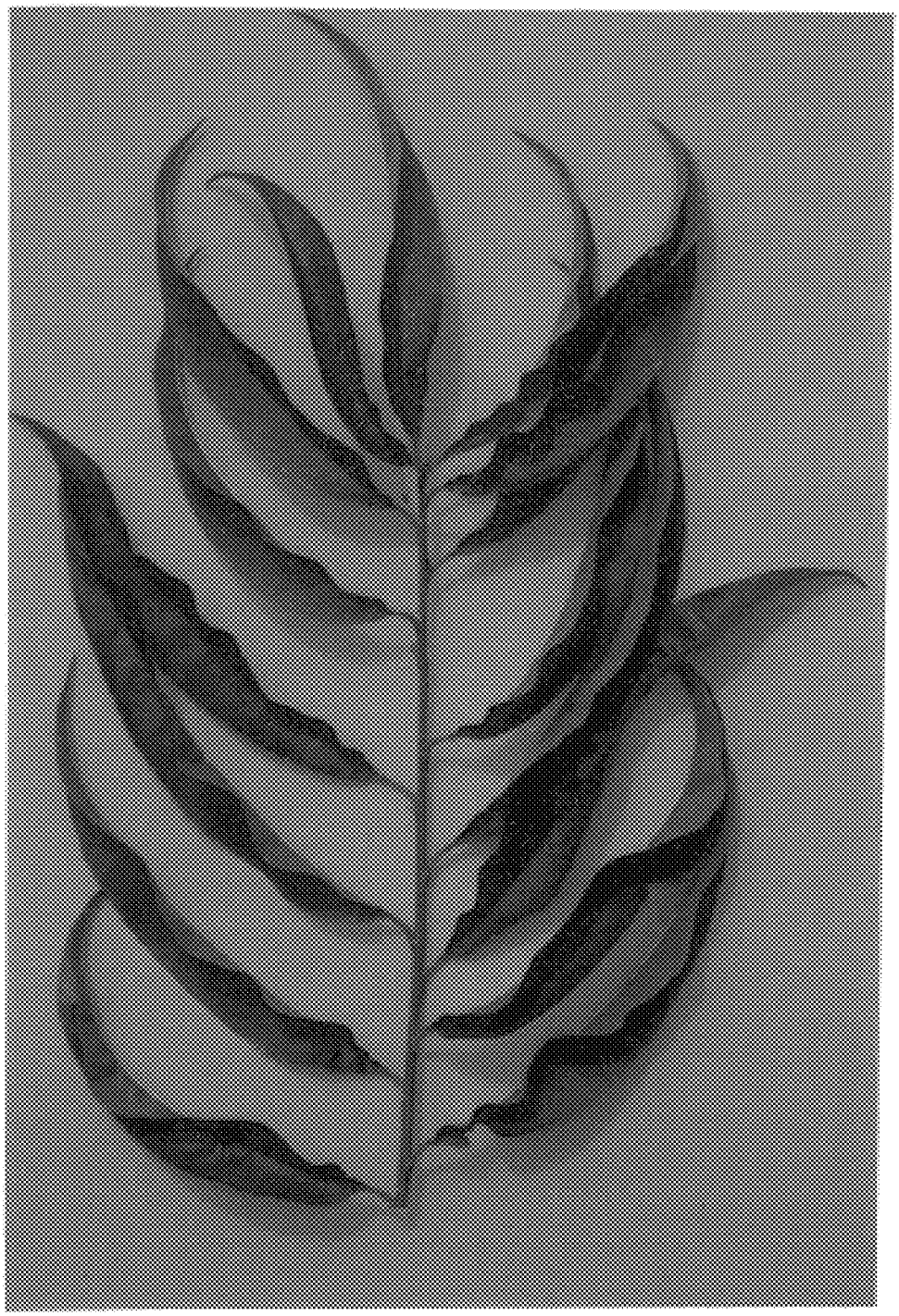
FIG. 4 shows the typical coloration and form of leaves of 'China Pearl' taken from a seven-year-old tree photographed on Jul. 13, 2000.
Figure 5:
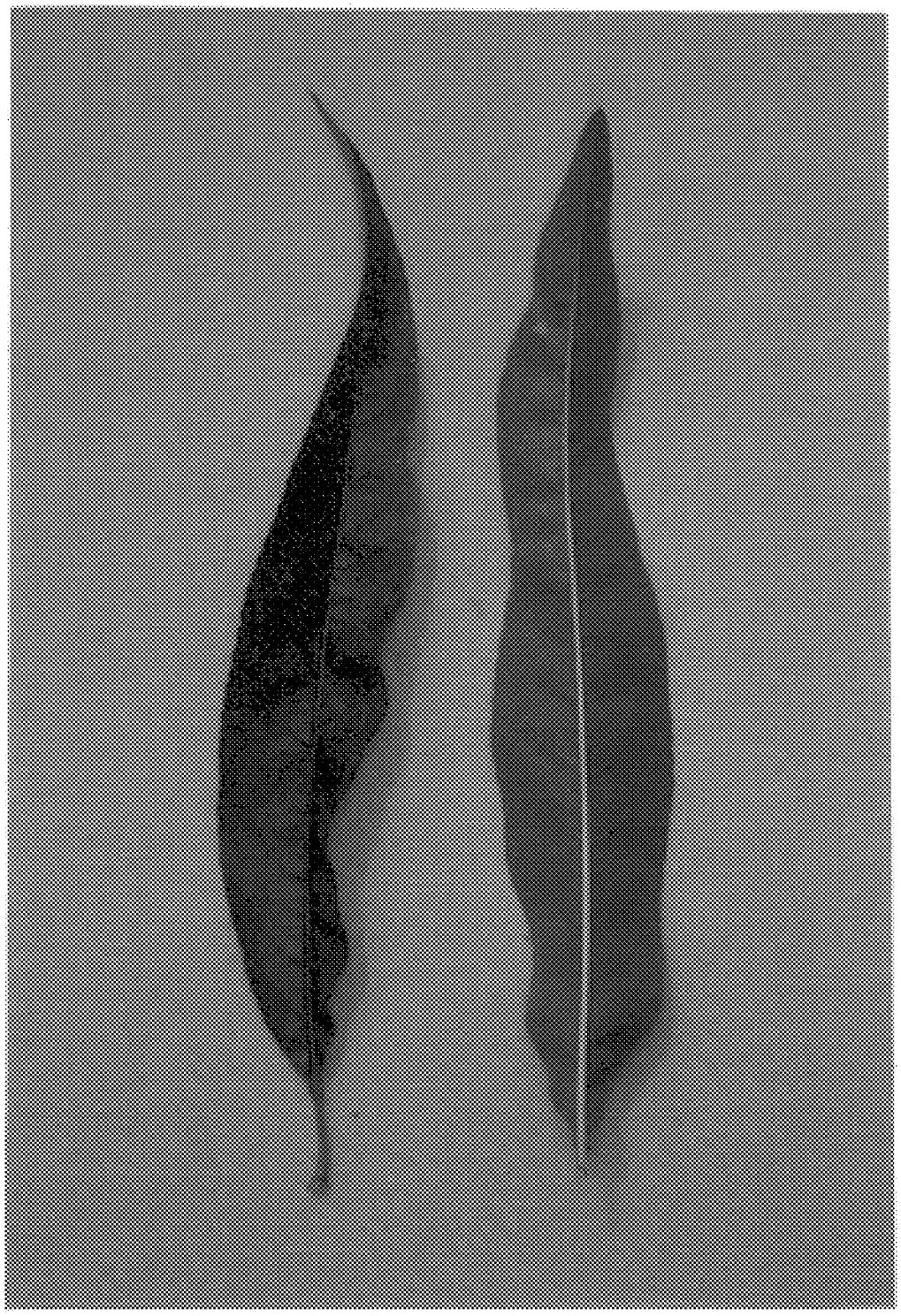
FIG. 5 shows a close-up of the upper (left) and lower (right) surface of leaves of 'China Pearl' photographed on Jul. 13, 2000.
Figure 6:
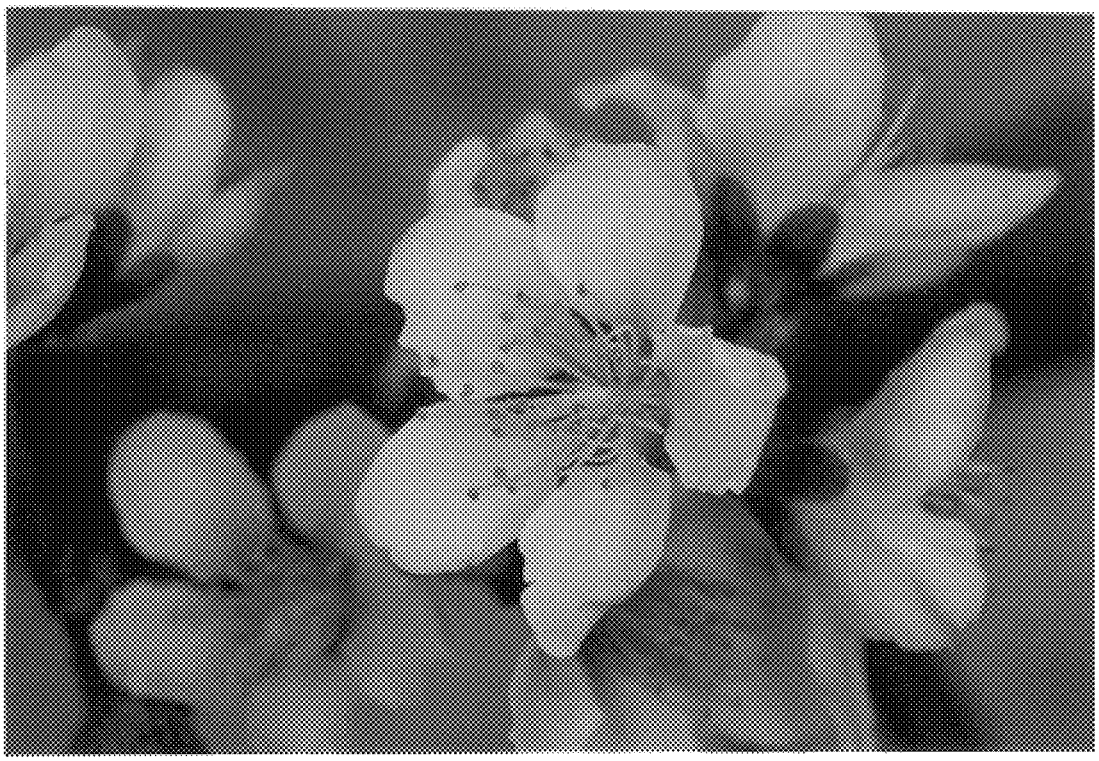
FIG. 6 shows the large petals and typical coloration of the flower, photographed on Mar. 17, 2000.

All photographs were taken from trees growing at the Sandhills Research Station, Jackson Springs, N.C. Color is as nearly true as it is reasonably possible to make in a color illustration of these characters.

DETAILED DESCRIPTION OF THE NEW VARIETY

The following is a detailed description of the botanical and pomological characteristics of the subject peach. Color data are presented in Royal Horticultural Society Colour chart designations. Where dimensions, sizes, colors and other characteristics are given, it is to be understood that such characteristics are approximations of averages set forth as accurately as practicable.

The descriptions reported herein are from specimens grown at Jackson Springs, N.C. unless otherwise noted.

Tree:

*Size.*—Large. Eight-year old tree average height 8.4 ft. Spread 13 ft. Trunk girth measured 1 foot above ground 5.8 in.

*Vigor.*—Very vigorous.

*Growth.*—Semi-upright.

*Production.*—High. Average of 3.3 bushels (143.6 lbs.) of fruit on 5-year-old trees.

*Crotch angles.*—Average branch angle between trunk and main branches 55 degrees.

Trunk:

*Size.*—Medium.

*Texture.*—Medium to rough.

*Color.*—Gray-brown 199-A.

Branches:

*Size.*—Medium.

*Surface.*—Smooth (new) to medium rough (old).

*Lenticels.*—Medium size. Medium number.

*Color.*—Bright green (new growth), grayish-orange (165-B. two-year-old branches), grayish-purple (183-B, one-year-old branches). Moderate red color on new growth.

Foliage:

*Leaves.*—Large. Mature leaf length 17.6 cm; width 3.6 cm.

*Form.*—Lanceolate. Acutely pointed.

*Thickness.*—Medium.

*Texture.*—Smooth to slightly rugose.

*Margin.*—Crenate.

*Petiole.*—Medium length, average=11 mm. Color yellow-green (146-C).

*Glands.*—Average number 3. Varies from 2 to 5. Located on base of leaf and upper portion of petiole. Small and reniform.

*Color.*—Upper surface — green to deep green (137-A). Lower surface — dull green (146-A).

*Density.*—Dense.

Flower buds:

*Size.*—Medium. Typical of peach.

*Width.*—Medium. (1.9 mm).

*Length.*—Medium. (4 mm).

*Pubescence.*—Lacking.

Flowers:

*Date of first bloom.*—March 10 to March 30. Varies yearly due to weather conditions.

*Size.*—Large, showy. Diameter=34 mm.

*Color.*—Petals medium red-purple (65-C). Calyx grayed purple (184-C).

*Reproductive organs.*—Stamens — erect, numerous. Pistils — usually one. Pollen—normal and abundant, yellow.

*Pollination requirements.*—Flowers self fertile.

*Number of flowers per bud.*—One.

*Number of petals per flower.*—Average 5.

*Pedicel.*—Short (2–3 mm). Color 142-C.

Fruit:

*Maturity.*—Late. Late July to early August. Average August 1.

*Size.*—Very large. Average 2.8 in. transverse diameter. Average 2.9 longitudinal diameter.

*Weight.*—Average of 53 mature fruit=6.9 ounces.

*Form.*—Round.

*Suture.*—Shallow to slightly grooved.

*Pubescence.*—Light.

*Skin color.*—50–60% red overcolor (41C to 42A) with yellow ground color (1C to 2C).

*Flesh color.*—Greenish-white (157-C), with little red intrusion (color 46-C) near the pit.

*Stone.*—Large, freestone. Color greyed-orange (175-A). Fresh weight=6.5 g. Size=36.6 mm height, 25.2 mm transverse diameter.

Titratable acidity.—0.27 malic acid equivalents, compared to 0.71 for variety 'Contender'.

*Soluble solids.*—13.5 to 14%.

*Eating quality.*—Excellent.

*Uses.*—Fresh consumption. Taste test evaluations have shown a preference by Oriental and Hispanic ethnic groups.

Disease reaction:

*Bacterial spot.*—Moderate resistance.

*Peach scab.*—Susceptible.

*Brown rot.*—Susceptible.

The variety: The most distinctive features of the variety are its very large, low acid, white flesh fruit, its late flowering (high chilling requirement), high resistance of flowers to cold temperature injury, and its moderate resistance to bacterial spot disease.

We claim:

1. A new and distinct variety of edible peach tree, substantially as illustrated and described, characterized by its very large, low acid fruit, its late flowering, its high resistance of flowers to cold temperatures, and its moderate resistance to bacterial spot disease.

* * * * *